United States Patent [19]
Elliott

[11] Patent Number: 6,114,359
[45] Date of Patent: Sep. 5, 2000

[54] ENDOTHELIN RECEPTOR ANTAGONISTS

[75] Inventor: John Duncan Elliott, Wayne, Pa.

[73] Assignee: SmithKline Beecham Corporation, Philadelphia, Pa.

[21] Appl. No.: 09/455,824

[22] Filed: Dec. 6, 1999

Related U.S. Application Data

[62] Division of application No. 09/142,510, Jul. 31, 1998, Pat. No. 6,022,886
[60] Provisional application No. 60/010,984, Feb. 1, 1996.
[51] Int. Cl.⁷ ....................... A61K 31/4439; A61P 13/12; C07D 401/14
[52] U.S. Cl. ........................ 514/338; 546/276.4; 548/562

[58] Field of Search .......................... 546/276.4; 548/562; 514/338

[56] References Cited

U.S. PATENT DOCUMENTS 3,063,978  11/1962  Lynn et al. .
3,678,063  7/1972  Binon et al. .

*Primary Examiner*—Robert W. Ramsuer
*Attorney, Agent, or Firm*—Linda E. Hall; Stephen A. Venetianer; Charles M. Kinzig

[57] ABSTRACT

Novel pyrroles, pyrazoles and triazoles, pharmaceutical compositions containing these compounds and their use as endothelin receptor agonists are described.

5 Claims, No Drawings

ENDOTHELIN RECEPTOR ANTAGONISTS

This application is a divisional of Ser. No. 09/142,510 filed Jul. 31, 1998 now U.S. Pat. No. 6,022,886 which claims the benefit of provision application Ser. No. 60/010,984 filed Feb. 1, 1996 and which is also a 371 of PCT/US97/00954 filed Jan. 31, 1997.

FIELD OF INVENTION

The present invention relates to pyrroles, pyrazoles and triazoles, pharmaceutical compositions containing these compounds and their use as endothelin receptor antagonists.

Endothelin (ET) is a highly potent vasoconstrictor peptide synthesized and released by the vascular endothelium. Endothelin exists as three isoforms, ET-1, ET-2 and ET-3. [Unless otherwise stated "endothelin" shall mean any or all of the isoforms of endothelin]. Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarction, subarachnoid hemorrhage, atherosclerosis, and patients with uraemia undergoing dialysis.

In vivo, endothelin has pronounced effects on blood pressure and cardiac output. An intravenous bolus injection of ET (0.1 to 3 nmol/kg) in rats causes a transient, dose-related depressor response (lasting 0.5 to 2 minutes) followed by a sustained, dose-dependent rise in arterial blood pressure which can remain elevated for 2 to 3 hours following dosing. Doses above 3 nmol/kg in a rat often prove fatal.

Endothelin appears to produce a preferential effect in the renal vascular bed. It produces a marked, long-lasting decrease in renal blood flow, accompanied by a significant decrease in GFR, urine volume, urinary sodium and potassium excretion. Endothelin produces a sustained antinatriuretic effect, despite significant elevations in atrial natriuretic peptide. Endothelin also stimulates plasma renin activity. These findings suggest that ET is involved in the regulation of renal function and is involved in a variety of renal disorders including acute renal failure, cyclosporine nephrotoxicity, radio contrast induced renal failure and chronic renal failure.

Studies have shown that in vivo, the cerebral vasculature is highly sensitive to both the vasodilator and vasoconstrictor effects of endothelin. Therefore, ET may be an important mediator of cerebral vasospasm, a frequent and often fatal consequence of subarachnoid hemorrhage.

ET also ex direct central nervous system effects such as severe apnea and ischemic lesions which suggests that ET may contribute to the development of cerebral infarcts and neuronal death.

ET has also been implicated in myocardial ischemia (Nichols et al. Br. J. Pharm. 99: 597–601, 1989 and Clozel and Clozel, Circ. Res., 65: 1193–1200, 1989) coronary vasospasm (Fukuda et al., Eur. J. Pharm. 165: 301–304, 1989 and Lüscher, Circ. 83: 701, 1991) heart failure, proliferation of vascular smooth muscle cells, (Takagi, Biochem & Biophys. Res. Commun.; 168: 537–543, 1990, Bobek et al., Am. J. Physiol. 258:408–C415, 1990) and atherosclerosis, (Nakaki et al., Biochem. & Biophys. Res. Commun. 158: 880–881, 1989, and Lerman et al., New Eng. J. of Med. 325: 997–1001, 1991). Increased levels of endothelin have been shown after coronary balloon angioplasty (Kadel et al., No. 2491 Circ. 82: 627, 1990).

Further, endothelin has been found to be a potent constrictor of isolated mammalian airway tissue including human bronchus (Uchida etal., Eur J. of Pharm. 154: 227–228 1988, LaGente, Clin. Exp. Allergy 20: 343–348, 1990; and Springall et al., Lancet, 337: 697–701, 1991). Endothelin may play a role in the pathogenesis of interstitial pulmonary fibrosis and associated pulmonary hypertension, Glard et al., Third International Conference on Endothelin, 1993, p. 34 and ARDS (Adult Respiratory Distress Syndrome), Sanai et al., Supra, p. 112.

Endothelin has been associated with the induction of hemorrhagic and necrotic damage in the gastric mucosa (Whittle etal., Br. J. Pharm. 95: 1011–1013, 1988); Raynaud's phenomenon, Cinniniello et al., Lancet 337: 114–115, 1991); Crohn's Disease and ulcerative colitis, Munch et al., Lancet, Vol. 339, p. 381; Migraine (Edmeads, Headache, Feb. 1991 p 127); Sepsis (Weitzberg et al., Circ. Shock 33: 222–227, 1991; Pittet et a;., Ann. Surg. 213: 262–264, 1991), Cyclosporin-induced renal failure or hypertension (Eur. J. Pharmacol., 180: 191–192, 1990, Kidney Int. 37: 1487–1491, 1990) and endotoxin shock and other endotoxin induced diseases (Biochem. Biophys. Res. Commun., 161: 1220–1227, 1989, Acta Physiol. Scand. 137: 317–318, 1989) and inflammatory skin diseases. (Clin Res. 41:451 and 484, 1993).

Endothelin has also been implicated in preclampsia of pregnancy. Clark et al., Am. J. Obstet. Gynecol. March 1992, p. 962–968; Kamor et al., N. Eng. J. of Med., Nov. 22, 1990, p. 1486–1487; Dekker et. al., Eur J. Ob. and Gyn. and Rep. Bio. 40 (1991) 215–220; Schiff et al., Am. J. Ostet. Gynecol. Feb. 1992, p. 624–628; diabetes mellitus, Takahashi et al., Diabetologia (1990) 33:306–310; and acute vascular rejection following kidney transplant, Watschinger et al., Transplantation Vol. 52, No. 4, pp. 743–746.

Endothelin stimulates both bone resorption and anabolism and may have a role in the coupling of bone remodeling. Tatrai et al. Endocrinology, Vol. 131, p. 603–607.

Endothelin has been reported to stimulate the transport of sperm in the uterine cavity, Casey et al., J. Clin. Endo and Metabolism, Vol. 74, No. 1, p. 223–225, therefore endothelin antagonists may be useful as male contraceptives. Endothelin modulates the ovarian/menstrual cycle, Kenegsberg, J. of Clin. Endo. and Met., Vol. 74, No. 1, p. 12, and may also play a role in the regulation of penile vascular tone in man, Lau et al., Asia Pacific J. of Pharm., 1991, 6:287–292 and Tejada et al., J. Amer. Physio. Soc, 1991, H1078–H1085. Endothelin also mediates a potent contraction of human prostatic smooth muscle, Langenstroer et al., J. Urology, Vol. 149, p. 495–499.

Thus, endothelin receptor antagonists would offer a unique approach toward the pharmacotherapy of hypertension, renal failure, ischernia induced renal failure, sepsis-endotoxin induced renal failure, prophylaxis and/or treatment of radio-contrast induced renal failure, acute and chronic cyclosporin induced renal failure, cerebrovascular disease, myocardial ischemia, angina, heart failure, asthma, pulmonary hypertension, pulmonary hypertension secondary to intrinsic pulmonary disease, atherosclerosis, Raynaud's phenomenon, ulcers, sepsis, migraine, glaucoma, endotoxin shock, endotoxin induced multiple organ failure or disseminated intravascular coagulation, cyclosporin-induced renal failure and as an adjunct in angioplasty for prevention of restenosis, diabetes, preclampsia of pregnancy, bone remodeling, kidney transplant, male contraceptives, infertility and priaprism and benign prostatic hypertrophy.

SUMMARY OF THE INVENTION

This invention comprises compounds represented by Formula (I) and pharmaceutical compositions containing these compounds, and their use as endothelin receptor antagonists which are useful in the treatment of a variety of cardiovascular and renal diseases including but not limited to: hypertension, acute and chronic renal failure, cyclosporine induced nephrotoxicity, benign prostatic hypertrophy, pulmonary hypertension, migraine, stroke, cerebrovascular vasospasm, myocardial ischemia, angina, heart failure, atherosclerosis, and as an adjunct in angioplasty for prevention of restenosis.

This invention further constitutes a method for antagonizing endothelin receptors in an animal, including humans, which comprises administering to an animal in need thereof an effective amount of a compound of Formula (I).

DETAILED DESCRIPTION OF THE INVENTION

The compounds of this invention are represented by structural Formula (I):

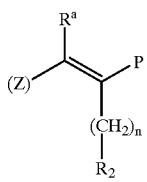

(I)

wherein (Z) is

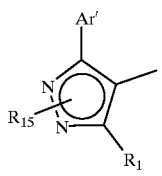 (d)

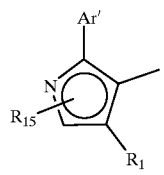 (e)

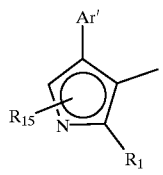 (f)

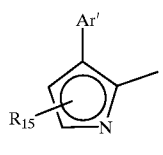 (g)

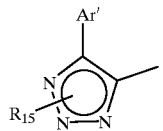 (h)

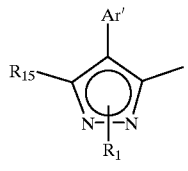 (i)

or

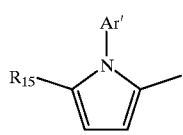 (j)

P is tetrazol-5-yl, $CO_2R_6$ or $C(O)N(R_6)S(O)_qR_{10}$;
$R^a$ is independently hydrogen or $C_{1-6}$alkyl;
$R_1$ is independently hydrogen, Ar or $C_{1-6}$alkyl;
$R_2$ is Ar, $C_{1-8}$alkyl, $C(O)R_{14}$ or —

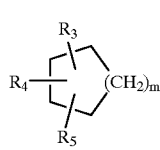 (c)

$R_3$ and $R_5$ are independently $R_{13}$ OH, $C_{1-8}$alkoxy, $S(O)_qR_{11}$, $N(R_6)_2$, Br, F, I, Cl, $CF_3$, $NHCOR_6R_{13}CO_2R_7$, $-X-R_9-Y$ or $-X(CH_2)_nR_8$ wherein each methylene group within $-X(CH_2)_nR_8$ may be unsubstituted or substituted by one or two $-(CH_2)_nAr$ groups;

$R_4$ is independently $R_{11}$, OH, $C_{1-5}$alkoxy, $S(O)_qR_{11}$, $N(R_6)_2$, Br, F, I, Cl or $NHCOR_6$, wherein the $C_{1-5}$-alkoxy may be unsubstituted or substituted by OH, methoxy or halogen;

$R_6$ is independently hydrogen or $C_{1-8}$alkyl;

$R_7$ is independently hydrogen, $C_{1-10}$alkyl, $C_{2-10}$loalkenyl or $C_{2-8}$alkynyl, all of which may be unsubstituted or substituted by one or more OH, $N(R_6)_2$, $CO_2R_{12}$, halogen or $XC_{1-10}$alkyl; or $R_7$ is $(CH_2)_nAr$;

$R_8$ is independently $R_{11}$, $CO_2R_7$, $CO_2C(R_{11})_2O(CO)XR_7$, $PO_3(R_7)_2$, $SO_2NR_7R_{11}$, $NR_7SO_2R_{11}$, $CONR_7SO_2R_{11}$, $SO_3R_7$, $SO_2R_7$, $P(O)(OR_7)R_7$, CN, $CO_2(CH_2)_mC(O)N(R_6)_2$, $C(R_{11})_2N(R_7)_2$, $C(O)N(R_6)_2$, tetrazole or $OR_6$;

$R_9$ is independently a bond, $C_{1-10}$alkylene, $C_{1-10}$alkenylene, $C_{1-10}$alkylidene, $C_{1-10}$alkynylene, all of which may be linear or branched, or phenylene, all of which may be unsubstituted or substituted by one of more OH, $N(R_6)_2$, COOH or halogen;

$R_{10}$ is independently $C_{1-10}$alkyl, $N(R_6)_2$ or Ar;

$R_{11}$ is independently hydrogen, Ar, $C_{1-8}$alkyl, $C_{2-8}$alkenyl, $C_{2-8}$alkynyl, all of which may be unsubstituted or substituted by one or more OH, $CH_2OH$, $N(R_6)_2$ or halogen;

$R_{12}$ is independently hydrogen, $C_{1-6}$alkyl, $C_{2-6}$alkenyl or $C_{2-7}$alkynyl;

$R_{13}$ is independently divalent Ar, $C_{1-10}$alkylene, $C_{1-10}$alkylidene, $C_{2-10}$alkenylene, all of which may be unsubstituted or substituted by one or more OH, $CH_2OH$, $N(R_6)_2$ or halogen;

$R_{14}$ is independently hydrogen, $C_{1-10}$alkyl, $XC_{1-10}$alkyl, Ar or XAr;

$R_{15}$ is independently hydrogen, Ar, $C_{1-6}$alkyl, or Xar;

$R_{16}$ is independently $C_{1-6}$alkyl or phenyl substituted by one or more $C_{1-6}$alkyl, OH, $C_{1-5}$alkoxy, $S(O)_q R_6$, $N(R_6)_2$, Br, F, I, Cl, $CF_3$ or $NHCOR_6$;

X is independently $(CH_2)_n$, O, $NR_6$ or $S(O)_q$;

Y is independently $CH_3$ or $X(CH_2)_n Ar$;

Ar is:

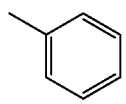

(a)

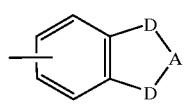

(b)

naphthyl, indolyl, furyl, oxazolyl, pyridyl, thienyl, oxazolidinyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $Z_1$ or $Z_2$ groups;

A is independently C=O, or $(C(R_6)_2)_m$;

D is independently —$CH_2$— or —O—;

$Z_1$ and $Z_2$ are independently hydrogen, $XR_6$, $C_{1-8}$alkyl, $(CH_2)_q CO_2 R_6$, $C(O)N(R_6)_2$, CN, $(CH_2)_n OH$, $NO_2$, F, Cl, Br, I, $N(R_6)_2$, $NHC(O)R_6$, $O(CH_2)_m C(O)NR_a SO_2 R_{15}$, $(CH_2)_m OC(O)NR_a SO_2 R_{16}$, $O(CH_2)_m NR_a C(O)NR_a SO_2 R_{16}$, $NR_7 C(O)NR_7 SO_2 R_{11}$, or tetrazolyl which may be substituted or unsubstituted by $C_{1-6}$alkyl, $CF_3$ or $C(O)R_6$;

Ar' is independently naphthyl, indolyl, furyl, oxazolyl, pyridyl, thienyl, oxazolidinyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $XR_9$—Y, $X(CH_2)_n R_8$, $Z_1$ or $Z_2$ groups;

m is independently 1 to 3;

n is independently 0 to 6;

q is, independently 0, 1 or 2;

provided $R_3$, $R_4$ and $R_5$ are not O—$O(CH_2)_n Ar$;

or a pharmaceutically acceptable salt thereof.

All alkyl, alkenyl, alkynyl and alkoxy groups may be straight or branched.

The compounds of the present invention may contain one or more asymmetric carbon atoms and may exist in racemic and optically active form. All of these compounds and diastereoisomers are contemplated to be within the scope of the present invention.

The preferred compounds are:

(E)-alpha-[[b 1-Butyl-5-[4[(2-carboxyphenyl)methoxy]-2-methoxypyrid-5-yl]-1H-pyrazol-4-yl]methylene]-6-methoxy-1,3-benzodioxole-5-propanoic acid;

(E)-alpha-[[1-Butyl-5-(3-carboxy-5-chlorothien-2-yl)-1H-pyrazolyl]methylene]-6-methoxy-1,3-benzodioxole-5-propanoic acid;

(E)-alpha-[[5-Butyl-4-[4[(2-carboxyphenyl)methoxy]-2-methoxypyrid-5-yl]-pyrrol-3-yl]methylene]-6-methoxy-1,3-benzodioxole-5-propanoic acid;

(E)-alpha-[[1-Butyl-2-[4-[(2-carboxyphenyl)methoxy]-2-methoxypyrid-5-yl]-pyrrol-3-yl]methylene]-6-methoxy-1,3-benzodioxole-5-propanoic acid;

(E)-alpha-[[5-Butyl-3-[(2-carboxyphenyl)methoxy]-5-chlorothien-2-yl)-1H-pyrazo-3-yl)methylene]-6methoxy-1,3-benzodioxole-5-propanoic acid;

(E)-alpha-[[5-Butyl-3-(3-carboxy-5-chlorofuran-2-yl)-1H-pyrazol-3-yl]methylene]-6-methoxy-1,3-benzodioxole-5-propanoic acid;

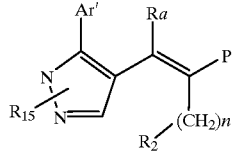

(Id)

Compounds of the Formula (Id), can be prepared starting from a ketone of Formula (2)

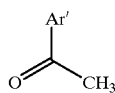

(2)

which can be reacted with dimethyl carbonate in the presence of a base such as sodium hydride at 40–70° C. to provide a keto ester of Formula (3).

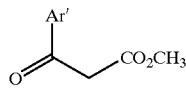

(3)

Reaction of keto ester of Formula (3) with N,N-dimethylformamide dimethyl acetal in hot toluene provided the enamine of Formula (4),

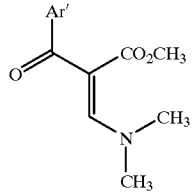

(4)

which was treated with a hydrazine derivative of Formula (5)

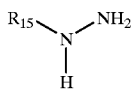
(5)

in a suitable solvent such as methanol or methanol/water mixture in the presence of a base such as sodium acetate to afford a substituted pyrazole of Formula (6).

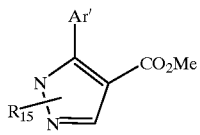
(6)

Reduction of the pyrazole of Formula (6) with diisobutylaluminum hydride at 0° C. in dichloromethane/toluene mixtures produced the pyrazolyl alcohol of Formula (7).

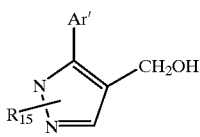
(7)

Oxidation of the primary alcohol of Formula (7) with Jones reagent at ambient temperature afforded the aldehyde of Formula (8).

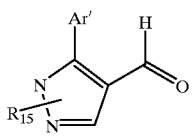
(8)

Knoevenagel condensation of pyrazolyl aldehyde of Formula (8) with a half acid of Formula (9), wherein $R_{16}$ is $C_{1-8}$ alkyl,

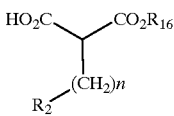
(9)

in a solvent such as benzene at reflux, in the presence of piperidinium acetate with azeotropic removal of water using a Dean-Stark apparatus afforded an ester of Formula (10).

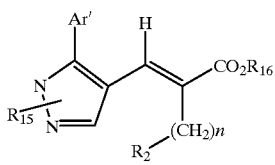
(10)

Saponification of an ester of Formula (10) using lithium hydroxide in a solvent such as aqueous methanol affords, after acidification with acetic acid, an acid of the Formula (Id), wherein P is $CO_2H$.

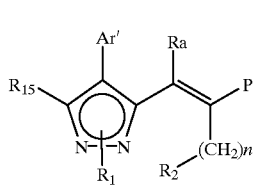
(Ii)

Compounds of Formula (Ii) can be prepared starting by commercially available ketones of Formula (11)

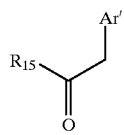
(11)

by reaction with diethyl oxalate of Formula (12)

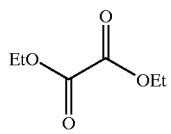
(12)

in the presence of a base such as sodium ethoxide in a solvent such as ethanol to produce a diketone of Formula (13).

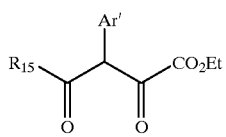
(13)

Reaction of a diketone of Formula (13) with hydrazine derivative of Formula (5) in a suitable solvent such as ethanol or ethanol/water at reflux provides a pyrazole of Formula (14)

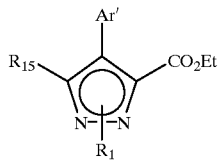
(14)

Reduction of the pyrazole of Formula (14) with diisobutylaluminum hydride at 0° C. in dichloromethane/toluene mixtures affords the primary alcohol of Formula (15).

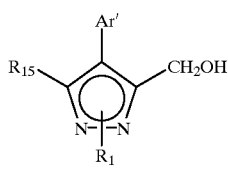
(15)

Oxidation of the pyrazolyl alcohol of Formula (15) with Jones reagent at ambient temperature provides the aldehyde of Formula (16);

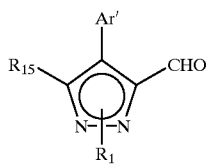
(16)

Knoevenagel condensation of pyrazolyl aldehyde of Formula (16) with a half acid of Formula (9), wherein $R_{16}$ is $C_{1-8}$ alkyl, in a solvent such as benzene at reflux, in the presence of piperidinium acetate with azeotropic removal of water affords an ester of Formula (17).

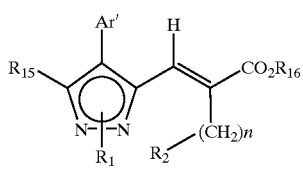
(17)

Saponification of an ester of Formula (17) using lithium hydroxide in a solvent such as aqueous methanol affords, after acidification with acetic acid, an acid of the Formula (Ii), wherein P is $CO_2H$ and $R_a$ is H.

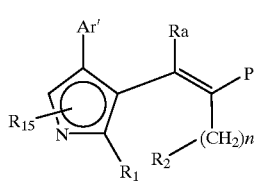
(If)

Compounds of Formula (If) can be prepared from the aryl ketone of Formula (18)

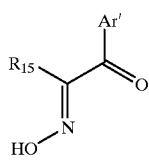
(18)

which can be converted into compound of Formula (19) by treatment with isobutyl nitrite and hydrochloric acid in diethyl ether

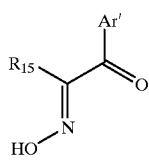
(19)

Hydrogenation of the isonitroso ketone of Formula (19) over palladium-on-charcoal catalyst in ethanol provided the alpha-amino ketone of Formula (20);

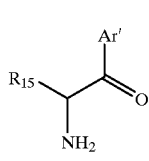
(20)

cyclocondensation of ketone of Formula (20) with ester of Formula (21), wherein $R_{16}$ is $C_{1-8}$ alkyl,

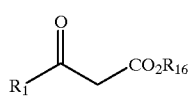
(21)

in a solvent such as acetic acid provides a pyrrole-3-carboxylate ester of Formula (22)

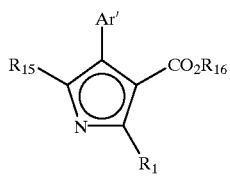
(22)

Reduction of compound of Formula (22) with diisobutylaluminum hydride at 0° C. in dichloromethane/toluene mixtures affords the alcohol of Formula (23).

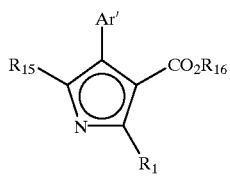
(23)

Oxidation of the primary alcohol of Formula (23) with Jones reagent at ambient temperature provides the aldehyde of Formula (24);

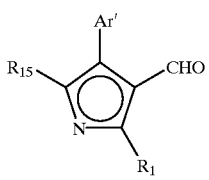
(24)

Knoevenagel condensation of pyrrolyl aldehyde of Formula (24) with a half acid of Formula (9), wherein $R_{16}$ is $C_{1-8}$ alkyl, in benzene at reflux, in the presence of piperidinium acetate with azeotropic removal of water using a Dean-Stark apparatus affords an ester of Formula (25).

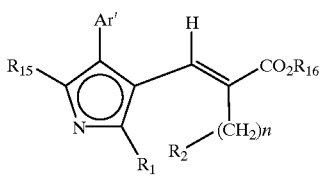
(25)

Saponification of an ester of Formula (25) with lithium hydroxide in a solvent such as aqueous methanol affords, after acidification with acetic acid, an acid of the Formula (If), wherein P is $CO_2H$ and $R_a$ is H.

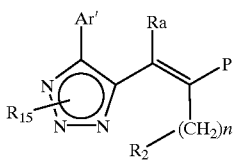
(Ih)

Compounds of Formula (Ih) can be prepared by reacting a keto ester of Formula (3) with an azide of Formula (26)

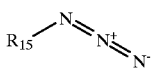
(26)

in methanol in the presence of a base such as sodium methoxide according to the procedure of L'Abbe et al (*J. Het Chem* 1970, 361–366) to provide a triazole of Formula (27).

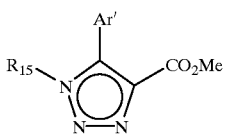
(27)

Reduction of the pyrazole of Formula (27) with diisobutylaluminum hydride in a mixture of dichloromethane/toluene at low temperature affords the primary alcohol of Formula (28).

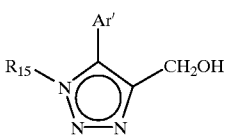
(28)

Oxidation of the pyrazolyl alcohol of Formula (28) with Jones reagent at ambient temperature provides the aldehyde of Formula (29),

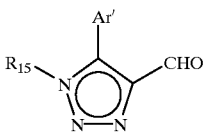
(29)

which was condensed with a half acid of Formula (9), in benzene at reflux, in the presence of piperidinium acetate with azeotropic removal of water to yield an ester of Formula (30).

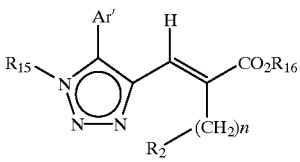
(30)

Saponification of an ester of Formula (30) using lithium hydroxide in a solvent such as aqueous methanol affords, after acidification with acetic acid, an acid of the Formula (Ih), wherein P is $CO_2H$ and $R_a$ is H.

Alternatively, a compound of Formula (27) can be obtained starting from dimethyl diazomalonate, of Formula (31),

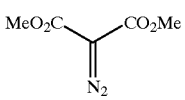
(31)

obtained from dimethyl malonate, p-toluenesulfonyl azide according to the procedure of Ledon (*Org Synth* VI, 414). Reaction of dimethyl diazomalonate with an amine of Formula (32)

(32)

provided a triazole of Formula (33).

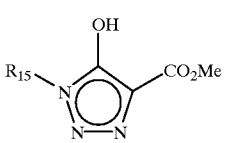
(33)

Conversion of compound of Formula (33) to a chloride of Formula (34) was achieved by treatment with phosphorus pentachloride in dichloromethane.

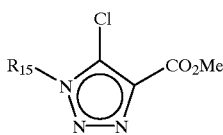

(34)

Coupling of compound of Formula (34) with boronic acid of Formula (35).

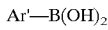

(35)

in the presence of a suitable base such as potassium carbonate with a palladium catalyst such as tetrakis(triphenylphosphine)palladium(0) in a mixture of toluene, ethanol and water at approximately 80–100° C. provided compounds of Formula of (27).

Boronic acids of Formula (35) were prepared by a process which comprises treating an aryl halide of Formula (36), where Z is I, Br, or Cl,

(36)

with an appropriate alkyllithium reagent such as n-butyllithium in tetrahydrofuran by addition of a borate such as triisopropyl borate and acidic work up.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (1) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the invention are administered in accordance with the present invention.

The biological activity of the compounds of Formula (I) are demonstrated by the following tests:

I. Binding Assay

A) CHO Cell Membrane Preparation

CHO cells stably transfected with human $ET_A$ and $ET_B$ receptors were grown in 245 mm×245 mm tissue culture plates in Dulbecco's modified Eagle's medium supplemented with 10% fetal bovine serum. The confluent cells were washed with Dulbecco's phosphate-buffered saline containing a protease inhibitor cocktail (5 mM EDTA, 0.5 mM PMSF, 5 ug/ml of leupeptin and 0.1 U/ml of aprotinin) and scraped in the same buffer. After centrifugation at 800× g, the cells were lysed by freezing in liquid nitrogen and thawing on ice followed by homogenization (30 times using a glass dounce homogenizer) in lysis buffer containing 20 mM Tris HCl, pH 7.5, and the protease inhibitor cocktail. After an initial centrifugation at 800× g for 10 nmin to remove unbroken cells and nuclei, the supernatants were centrifuged at 40,000× g for 15 min and the pellet was resuspended in 50 mM Tris HCl, pH 7.5, and 10 mM $MgCl_2$ and stored in small aliquots at −70° C. after freezing in liquid $N_2$. Protein was determined by using the BCA method and BSA as the standard.

(B) Binding Studies $[^{125}I]ET$-1 binding to membranes prepared from CHO cells was performed following the procedure of Elshourbagy et al. (1993). Briefly, the assay was initiated in a 100 ul volume by adding 25 ul of $[^{125}I]Et$-1 (0.2–0.3 nM) in 0.05% BSA to membranes in the absence (total binding) or presence (nonspecific binding) of 100 nM unlabeled ET-1. The concentrations of membrane proteins were 0.5 and 0.05 ug per assay tube for $ET_A$ and $ET_B$ receptors, respectively. The incubations (30° C., 60 min) were stopped by dilution with cold buffer (20 mM Tris HCl. pH 7.6, and 10 mM $MgCl_2$) and filtering through Whatman GF/C filters (Clifton, N.J.) presoaked in 0.1% BSA. The filters were washed 3 times (5 ml each time) with the same buffer by using a Brandel cell harvester and were counted by using a gamma counter at 75% efficiency.

The following example is illustrative and is not limiting of the compounds of this invention.

EXAMPLE 1

Formulations for pharmaceutical use incorporating compounds of the present invention can be prepared in various forms and with numerous excipients. Examples of such formulations are given below.

Inhalant Formulation

A compound of Formula I, (1 mg to 100 mg) is aerosolized from a metered dose inhaler to deliver the desired amount of drug per use.

| Tablets/Ingredients | Per Tablet |
| --- | --- |
| 1. Active ingredient (Cpd of Form. I) | 40 mg |
| 2. Corn Starch | 20 mg |
| 3. Alginic acid | 20 mg |
| 4. Sodium Alginate | 20 mg |
| 5. Mg stearate | 1.3 mg |
| | 2.3 mg |

Procedure for Tablets

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its conversion to wet granules.

Step 3 The wet mass is converted to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5.

Step 6 The lubricated granules are compressed on a suitable tablet press.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then steriled by filtration through a 0.22 micron membrane filter and sealed in sterile containers.

What is claimed is:

1. A compound of Formula (I):

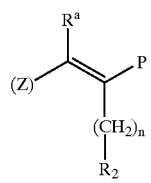

(I)

wherein (Z) is

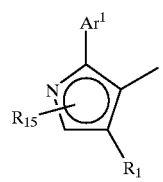

(e)

(f)

(g)

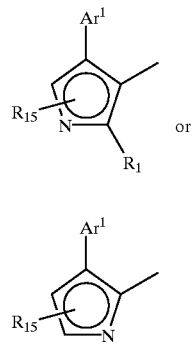

P is tetrazol-5-yl, $XO_2R_6$ or $C(O)N(R_6)S(O)_1R_{10}$;

$R^a$ is independently hydrogen or $C_{1-6}$alkyl;

$R_1$ is independently hydrogen, Ar or $C_{1-6}$alkyl;

$R_2$ is Ar, $C_{1-8}$alkyl, $C(O)R_{14}$ or

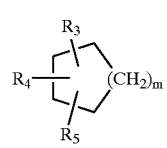

(c)

$R_3$ and $R_5$ are independently $R_{13}$ OH, $C_{1-8}$alkoxy, $S(O)_q R_{11}$, $N(R_6)_2$, Br, F, I, Cl, $CF_3$, $NHCOR_6$ $R_{13}CO_2R_7$, —X—$R_9$—Y or —$X(CH_2)_{11}R_8$ wherein each methylene group within —$X(CH_2)_nR_8$ may be unsubstituted or substituted by one or two —$(CH_2)_nAr$ groups;

$R_4$ is independently $R_{11}$, OH, $C_{1-5}$alkoxy, $S(O)_q R_{11}$, $N(R_6)_2$, Br, F, I, Cl or $NHCOR_6$, wherein the $C_{1-5}$alkoxy may be unsubstituted or substituted by OH, methoxy or halogen;

$R_6$ is independently hydrogen or $C_{1-8}$alkyl;

$R_7$ is independently hydrogen, $C_{1-10}$alkyl, $C_{2-10}$alkenyl or $C_{2-8}$alkynyl, all of which may be unsubstituted or substituted by one or more OH, $N(R_6)_2$, $CO_2R_{12}$, halogen or $XC_{1-10}$alkyl; or $R_7$ is $(CH_2)_nAr$;

R$_8$ is independently R$_{11}$, CO$_2$R$_7$, CO$_2$C(R$_{11}$)$_2$O(CO)XR$_7$, PO$_3$(R$_7$)$_2$, SO$_2$NR$_7$R$_{11}$, NR$_7$SO$_2$R$_{11}$, CONR$_7$SO$_2$R$_{11}$, SO$_3$R$_7$, SO$_2$R$_7$, P(O)(OR$_7$)R$_7$, CN, CO$_2$(CH$_2$)$_m$C(O)N(R$_6$)$_2$, C(R$_{11}$)$_2$N(R$_7$)$_2$, C(O)N(R$_6$)$_2$, tetrazole or OR$_6$;

R$_9$ is independently a bond, C$_{1-10}$alkylene, C$_{1-10}$alkenylene, C$_{1-10}$alkylidene, C$_{1-10}$alkynylene, all of which may be linear or branched, or phenylene, all of which may be unsubstituted or substituted by one or more OH, N(R$_6$)$_2$, COOH or halogen;

R$_{10}$ is independently C$_{1-10}$alkyl, N(R$_6$)$_2$ or Ar;

R$_{11}$ is independently hydrogen, Ar, C$_{1-8}$alkyl, C$_{2-8}$alkenyl, C$_{2-8}$alkynyl, all of which may be unsubstituted or substituted by one or more OH, CH$_2$OH, N(R$_6$)$_2$ or halogen;

R$_{12}$ is independently hydrogen, C$_{1-6}$alkyl, C$_{2-6}$alkenyl or C$_{2-7}$alkynyl;

R$_{13}$ is independently divalent Ar, C$_{1-10}$alkylene, C$_{1-10}$alkylidene, C$_{2-10}$alkenylene, all of which may be unsubstituted or substituted by one or more OH, CH$_2$OH, N(R$_6$)$_2$ or halogen;

R$_{14}$ is independently hydrogen, C$_{1-10}$alkyl, XC$_{1-10}$alkyl, Ar or XAr;

R$_{15}$ is independently hydrogen, Ar, C$_{1-6}$alkyl, or XAr;

R$_{16}$ is independently C$_{1-6}$alkyl or phenyl substituted by one or more C$_{1-6}$alkyl, OH, C$_{1-5}$alkoxy, S(O)$_q$R$_6$, N(R$_6$)$_2$, Br, F, I, Cl, CF$_3$ or NHCOR$_6$;

X is independently (CH$_2$)$_n$, O, NR$_6$ or S(O)$_q$;

Y is independently CH$_3$ or X(CH$_2$)$_n$Ar;

Ar is:

(a)

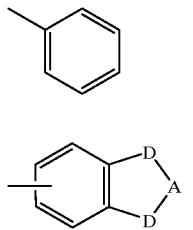

(b)

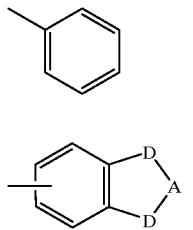

naphthyl, all of which may be unsubstituted or substituted by one or more Z$_1$ or Z$_2$ groups;

A is independently C≡O, or (C(R$_6$)$_2$)$_m$;

D is independently —CH$_2$— or —O—;

Z$_1$ and Z$_2$ are independently hydrogen, XR$_6$, C$_{1-8}$alkyl, (CH$_2$)$_q$CO$_2$R$_6$, C(O)N(R$_6$)$_2$, CN, (CH$_2$)$_n$OH, NO$_2$, F, Cl, Br, I, N(R$_6$)$_2$, NHC(O)R$_6$, O(CH$_2$)$_m$C(O)NR$_1$SO$_2$R$_{15}$, (CH$_2$)$_m$OC(O)NR$_a$SO$_2$R$_{16}$, O(CH$_2$)$_m$NR$_a$C(O)NR$_a$SO$_2$R$_{16}$, NR$_7$C(O)NR$_7$SO$_2$R$_{11}$, or tetrazolyl which may be substituted or unsubstituted by C$_{1-6}$alkyl, CF$_3$ or C(O)R$_6$;

Ar' is independently naphthyl, indolyl, faryl, oxazolyl, pyridyl thienyl, oxazolidinyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyridyl; all of which may be unsubstituted or substituted by one or more XR$_9$—Y, X(CH$_2$)$_n$R$_8$, Z$_1$ or Z$_2$ groups;

m is independently 1 to 3;

n is independently 0 to 6;

q is independently 0, 1 or 2;

provided R$_3$, R$_4$ and R$_5$ are not O—O(CH$_2$)$_n$Ar;

or a pharmaceutically acceptable salt thereof.

2. A pharmaceutical composition comprising a compound of claim 1 and a pharmaceutically acceptable carrier.

3. A method of treatment of diseases caused by an excess of endothelin comprising administering to a subject in need thereof, an effective amount of an endothelin receptor antagonist of claim 1.

4. A method of treating renal failure, hypertension, pulmonary hypertension or heart failure which comprises administering to a subject in need thereof, an effective amount of a compound of claim 1.

5. A compound of claim 1 selected from the group consisting of:

(E)-alpha-[[5-Butyl-4-[4-[(2-carboxyphenyl)methoxy]-2-methoxypyrid-5-yl]-pyrrol-3-yl]methylene]-6-methoxy-1,3-benzodioxole-5-propanoic acid; or (E)-alpha-[[1-Butyl-2-[4-[(2-carboxyphenyl)methoxy]-2-methoxypyrid-5-yl]-pyrrol-3-yl]methylene]-6-methoxy-1,3-benzodioxole-5-propanoic acid.

* * * * *